United States Patent
Wang

(10) Patent No.: US 9,297,036 B2
(45) Date of Patent: Mar. 29, 2016

(54) NUCLEIC ACID PROBES FOR ANALYSIS OF SMALL RNAS AND OTHER POLYNUCLEOTIDES

(75) Inventor: Hui Wang, Loveland, CO (US)

(73) Assignee: AGILENT TECHNOLOGIES, INC, Santa Clara, CA (US)

( * ) Notice: Subject to any disclaimer, the term of this patent is extended or adjusted under 35 U.S.C. 154(b) by 1687 days.

(21) Appl. No.: 11/173,693

(22) Filed: Jul. 1, 2005

(65) Prior Publication Data

US 2007/0003940 A1 Jan. 4, 2007

(51) Int. Cl.
| | |
|---|---|
| C12M 1/34 | (2006.01) |
| C12Q 1/68 | (2006.01) |
| C07H 21/02 | (2006.01) |
| C07H 21/04 | (2006.01) |
| G01N 31/22 | (2006.01) |
| G01N 33/52 | (2006.01) |

(52) U.S. Cl.
CPC .................................. C12Q 1/6837 (2013.01)

(58) Field of Classification Search
CPC ......... C12Q 1/68; C12Q 1/6837; C12M 1/34; C07H 21/02; C07H 21/04; G01N 31/22; G01N 33/52
USPC ............. 435/6.1, 6.11, 287.2; 536/23.1, 24.3; 422/430
See application file for complete search history.

(56) References Cited

U.S. PATENT DOCUMENTS

| | | | |
|---|---|---|---|
| 5,556,752 A * | 9/1996 | Lockhart et al. | 506/16 |
| 5,719,028 A * | 2/1998 | Dahlberg et al. | 435/6 |
| 5,770,365 A | 6/1998 | Lane et al. | |
| 6,194,149 B1 * | 2/2001 | Neri et al. | 435/6.18 |
| 6,355,423 B1 | 3/2002 | Rothberg et al. | |
| 6,423,535 B1 | 7/2002 | Arnold et al. | |
| 6,660,480 B2 | 12/2003 | Ramsey et al. | |
| 6,794,499 B2 | 9/2004 | Wengel et al. | |
| 7,544,793 B2 * | 6/2009 | Gao et al. | 536/25.3 |
| 2002/0006617 A1 * | 1/2002 | Fan et al. | 435/6 |
| 2003/0003490 A1 * | 1/2003 | Fan et al. | 435/6 |
| 2003/0022207 A1 | 1/2003 | Balasubramanian et al. | |
| 2005/0037362 A1 | 2/2005 | Remacle et al. | |
| 2005/0266418 A1 * | 12/2005 | Chen et al. | 435/6 |
| 2007/0003937 A1 | 1/2007 | Wang | |
| 2007/0099193 A1 | 5/2007 | Wang | |
| 2007/0172845 A1 | 7/2007 | Wang | |

FOREIGN PATENT DOCUMENTS

| | | | |
|---|---|---|---|
| CA | WO 01/94625 | * | 12/2001 |
| WO | WO9401550 A1 | | 1/1994 |
| WO | 97 08183 | | 3/1997 |
| WO | WO 97/08183 | * | 3/1997 |
| WO | 01 57248 | | 8/2001 |
| WO | 2004078946 | | 9/2004 |
| WO | 2004081520 | | 9/2004 |
| WO | WO2005003318 A2 | | 1/2005 |
| WO | 2005047301 | | 5/2005 |

OTHER PUBLICATIONS

Huang et al, A simple method for 3' labeleing of RNA, 1996, Nucleic Acids Research, 24, 4360-4361.*
Gao et al, Making nucleic acid sequences in parallel and use, Mar. 1, 2005, Secification—U.S. Appl. No. 60/657,304, filed Mar. 1, 2005, pp. 1-27.*
Gao et al , Making nucleic acid sequence in parallel and use, Mar. 1, 2005, Drawings—60/657,304, filed Mar. 1, 2005, pp. 1-17.*
Liu et al, An oligonucleotide microchip for genome wide microRNA profiling in human and mouse tisues, 2004, PNAS, 101, 9740-9744.*
Ahern, Biochemical, Reagents Kits Offer Scientists Good Return On Investment, 1995, The Scientist, 9, p. 20 (1-7).*
Walter et al, Coaxial stacking of helixes enhances binding of oligoribonucleotides and improves predictions of RNA folding, 1994, PNAS, 91, 9218-9222.*
Partial European Search Report dated Oct. 31, 2006.
Amy E. Walter et al—"Coaxial Stacking Of Helixes Enhances Binding of Oligoribonucleotides And Improves Predictions of RNA Folding"; Proceedings of the National Academy of Sciences of the United States of America, vol. 91, No. 20, 1994, pp. 9218-9222; XP 002404916.
Chang-Gong Liu et al—"An Oligonucleotide Microchip For Genome-Wide MicroRNA Profiling in Human and Mouse Tissues"; Proceedings of The National Academy of Sciences of USA, National Academy of Science, Washington DC, US, vol. 101, No. 26, Jun. 29, 2004, pp. 9740-9744; XP002364908.
P. V. Riccelli et al—"Hybridization of Single-Stranded DNA Targets to Immobilized Complementary DNA Probes: Comparison of Hairpin Versus Linear Capture Probes"; Nucleic Acids Research, Oxford University Press, Surrey, GB, vol. 29, No. 4, Feb. 15, 2001, pp. 996-1004; XP002282478.

(Continued)

*Primary Examiner* — Narayan Bhat

(57) ABSTRACT

The invention provides a nucleic acid probe for detecting a polynucleotide. The probe contains a region that base-pairs with a polynucleotide to form a duplex and a $T_m$ enhancement domain that increases the stability of the duplex. The $T_m$ enhancement domain may contain a nucleotide clamp and/or a hairpin structure, for example. Also provided is an array of subject nucleic acid probes bound to a surface of the solid support. Methods of using a subject probe to assess polynucleotides, e.g., small RNAs in a sample are provided, as are kits for use in practicing the subject methods.

14 Claims, 3 Drawing Sheets

(56) References Cited

OTHER PUBLICATIONS

Walter et al. "Coaxial Stacking of Helixes Enhances Binding of Oligoribonucleotides and Improves Predictions of RNA Folding," 1994, Proc. Natl. Acad. Sci. USA, 91:9218-9222.
Novina et al. "The RNAi Revolution," 2004 Nature, 430:161-164.
Griffiths-Jones, " The MicroRNA Registry," 2004, Nucleic Acids Reseach, 32:D109-D111.
Baskerville et al. "Micorarray Profiling of MicroRNAs Reveals Frequent Coexpression With Neighboring miRNAs and Host Genes," 2005, RNA 11:241-247.
Ambros et al. "A Uniform System for MicroRNA Annotation," 2003, RNA, 9:277-279.
Aravin, A., et al. Identification and characterization of small RNAs involved in RNA silencing. FEBS Letters. 2005, vol. 579, pp. 5830-5840.
Babak, T., et al. Probing microRNAs with microarrays: Tissue specificity and functional inference. RNA. 2004, vol. 10, pp. 1813-1819.
Thomson, J., et al. A custom microarray platform for analysis of microRNA gene expression. Nature Methods. 2004, vol. 1, No. 1, pp. 47-53.

* cited by examiner

NUCLEIC ACID PROBES FOR ANALYSIS OF SMALL RNAS AND OTHER POLYNUCLEOTIDES

BACKGROUND OF THE INVENTION

Since the discovery of the biological activity of short interfering RNAs (siRNAs) over a decade ago, so called "small RNAs" (i.e., short non-coding regulatory RNAs that have a defined sequence) have become a subject of intense interest in the research community. Exemplary short RNAs include siRNAs, microRNAs (miRNAs), tiny non-coding RNAs (tncRNAs) and small modulatory RNAs (smRNAs), as well as many others.

Although the exact biological fuinctions of most small RNAs remain a mystery, it is clear that they are abundant in plants and animals. For example, to date, over 78 *Drosophila* microRNA species and 200 human microRNA species have been identified. The levels of the individual species of small RNA, in particular microRNA species, appears to vary according to the developmental stage and type of tissue being examined. It is thought that the levels of particular small RNAs may be correlated with particular phenotypes, as well as with the levels of particular mRNAs and proteins. Further, viral microRNAs have been identified, and their presence has been linked to viral latency.

Methods that provide for quantitative detection of small RNAs are therefore extremely valuable. To this end, a considerable amount of effort is currently being put into developing array platforms to facilitate the analysis of small RNAs, particularly microRNAs.

However, in order to perform array experiments that provide quantitative results, it is highly desirable to use an array that contains probes that have similar melting temperatures ($T_m$s) to each other. This presents a challenge for the design of arrays for the analysis of small RNAs because certain small RNAs are very short (e.g., in the range of 19-21 nucleotides in length), severely limiting the choices of sequences that can be employed in a probe for those small RNAs. Further, prior art small RNA detection methods may not discriminate between the small RNA and the precursor RNAs from which they are made, leading to results that do not accurately reflect the actual amount of a small RNA in a sample.

In view of the above, there is a great need for improved polynucleotide probes, particularly sets of polynucleotide probes having similar $T_m$s, for assessing small RNAs in a sample. The invention described herein meets this need, and others.

LITERATURE OF INTEREST

Literature of interest includes: Novina et al, Nature 2004 430:161-164; Liu et al, Proc. Natl. Acad. Sci. 2004 101:9740-9744; Thomson et al, Nature Methods 2004 1:1-7; Babak et al, RNA 2004 10:1813-1819; Pfeffer et al, Science 2004 304:734-736; Nelson et al, Science 2001 294:88-862; Liu et al, Nanobiology 1999; 4: 257-262; Walter et al, Proc. Natl. Acad. Sci. 1994 91:9218-9222; Ambros et al RNA 2003 9:277-279; Baskerville et al RNA 2005 11:241-247; and Griffiths-Jones, Nucl. Acids Res. 2004 32:D109-D111.

SUMMARY OF THE INVENTION

The invention provides a nucleic acid probe for detecting a polynucleotide, e.g., a small RNA, in a sample. The probe contains a region that base-pairs with a polynucleotide to form a duplex and a $T_m$ enhancement domain that increases the stability of the duplex. The $T_m$ enhancement domain may contain a nucleotide clamp and/or a hairpin structure, for example. Also provided is an array of subject nucleic acid probes bound to a surface of the solid support. Methods of using a subject probe to assess polynucleotides in a sample are provided, as are kits for use in practicing the subject methods. The invention finds use in a wide variety of diagnostic and research applications.

DEFINITIONS

Figure 1:
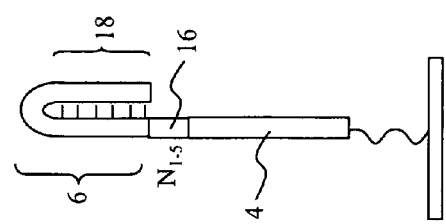
FIG. 1 schematically illustrates a nucleic acid probe of the invention.

The term "nucleic acid" and "polynucleotide" are used interchangeably herein to describe a polymer of any length, e.g., greater than about 10 bases, greater than about 100 bases, greater than about 500 bases, greater than 1000 bases, usually up to about 10,000 or more bases composed of nucleotides, e.g., deoxyribonucleotides or ribonucleotides, or compounds produced synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Naturally-occurring nucleotides include guanine, cytosine, adenine and thymine (G, C, A and T, respectively).

The terms "ribonucleic acid" and "RNA" as used herein mean a polymer composed of ribonucleotides.

The terms "deoxyribonucleic acid" and "DNA" as used herein mean a polymer composed of deoxyribonucleotides.

The term "oligonucleotide" as used herein denotes a single stranded multimer of nucleotide of from about 10 to 100 nucleotides. Oligonucleotides are usually synthetic and, in many embodiments, are under 60 nucleotides in length.

The term "oligomer" is used herein to indicate a chemical entity that contains a plurality of monomers. As used herein, the terms "oligomer" and "polymer" are used interchangeably, as it is generally, although not necessarily, smaller "polymers" that are prepared using the functionalized substrates of the invention, particularly in conjunction with combinatorial chemistry techniques. Examples of oligomers and polymers include polydeoxyribonucleotides (DNA), polyribonucleotides (RNA), other nucleic acids that are C-glycosides of a purine or pyrimidine base, polypeptides (proteins), polysaccharides (starches, or polysugars), and other chemical entities that contain repeating units of like chemical structure.

The term "sample" as used herein relates to a material or mixture of materials, typically, although not necessarily, in fluid form, containing one or more components of interest.

The terms "nucleoside" and "nucleotide" are intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like.

The phrase "surface-bound nucleic acid" refers to a nucleic acid that is immobilized on a surface of a solid substrate, where the substrate can have a variety of configurations, e.g., a sheet, bead, or other structure. In certain embodiments, the nucleic acid probes employed herein are present on a surface of the same planar support, e.g., in the form of an array.

The phrase "labeled population of nucleic acids" refers to mixture of nucleic acids that are detectably labeled, e.g., fluorescently labeled, such that the presence of the nucleic acids can be detected by assessing the presence of the label.

The term "array" encompasses the term "microarray" and refers to an ordered array presented for binding to nucleic acids and the like.

An "array," includes any two-dimensional or substantially two-dimensional (as well as a three-dimensional) arrangement of spatially addressable regions bearing nucleic acids, particularly oligonucleotides or synthetic mimetics thereof, and the like, e.g., UNA otigonucleotides. Where the arrays are arrays of nucleic acids, the nucleic acids may be adsorbed, physisorbed, chemisorbed, or covalently attached to the arrays at any point or points along the nucleic acid chain.

Any given substrate may carry one, two, four or more arrays disposed on a surface of the substrate. Depending upon the use, any or all of the arrays may be the same or different from one another and each may contain multiple spots or features. A typical array may contain one or more, including more than two, more than ten, more than one hundred, more than one thousand, more ten thousand features, or even more than one hundred thousand features, in an area of less than 20 $cm^2$ or even less than 10 $cm^2$, e.g., less than about 5 $cm^2$, including less than about 1 $cm^2$, less than about 1 $mm^2$, e.g., 100 $\mu m^2$, or even smaller. For example, features may have widths (that is, diameter, for a round spot) in the range from a 10 µm to 1.0 cm. In other embodiments each feature may have a width in the range of 1.0 µm to 1.0 mm, usually 5.0 µm to 500 µm, and more usually 10 µm to 200 µm. Non-round features may have area ranges equivalent to that of circular features with the foregoing width (diameter) ranges. At least some, or all, of the features are of different compositions (for example, when any repeats of each feature composition are excluded the remaining features may account for at least 5%, 10%, 20%, 50%, 95%, 99% or 100% of the total number of features). Inter-feature areas will typically (but not essentially) be present which do not carry any nucleic acids (or other biopolymer or chemical moiety of a type of which the features are composed). Such inter-feature areas typically will be present where the arrays are formed by processes involving drop deposition of reagents but may not be present when, for example, photolithographic array fabrication processes are used. It will be appreciated though, that the inter-feature areas, when present, could be of various sizes and configurations.

Each array may cover an area of less than 200 $cm^2$, or even less than 50 $cm^2$, 5 $cm^2$, 1 $cm^2$, 0.5 $cm^2$, or 0.1 $cm^2$. In certain embodiments, the substrate carrying the one or more arrays will be shaped generally as a rectangular solid (although other shapes are possible), having a length of more than 4 mm and less than 150 mm, usually more than 4 mm and less than 80 mm, more usually less than 20 mm; a width of more than 4 mm and less than 150 mm, usually less than 80 mm and more usually less than 20 mm; and a thickness of more than 0.01 mm and less than 5.0 mm, usually more than 0.1 mm and less than 2 mm and more usually more than 0.2 and less than 1.5 mm, such as more than about 0.8 mm and less than about 1.2 mm. With arrays that are read by detecting fluorescence, the substrate may be of a material that emits low fluorescence upon illumination with the excitation light. Additionally in this situation, the substrate may be relatively transparent to reduce the absorption of the incident illuminating laser light and subsequent heating if the focused laser beam travels too slowly over a region. For example, the substrate may transmit at least 20%, or 50% (or even at least 70%, 90%, or 95%), of the illuminating light incident on the front as may be measured across the entire integrated spectrum of such illuminating light or alternatively at 532 nm or 633 nm.

Arrays can be fabricated using drop deposition from pulse-jets of either precursor units (such as nucleotide or amino acid monomers) in the case of in situ fabrication, or the previously obtained nucleic acid. Such methods are described in detail in, for example, the previously cited references including U.S. Pat. Nos. 6,242,266, 6,232,072, 6,180,351, 6,171,797, 6,323,043, U.S. patent application Ser. No. 09/302,898 filed Apr. 30, 1999 by Caren et al., and the references cited therein. As already mentioned, these references are incorporated herein by reference. Other drop deposition methods can be used for fabrication, as previously described herein. Also, instead of drop deposition methods, photolithographic array fabrication methods may be used. Inter-feature areas need not be present particularly when the arrays are made by photolithographic methods as described in those patents.

An array is "addressable" when it has multiple regions of different moieties (e.g., different oligonucleotide sequences) such that a region (i.e., a "feature" or "spot" of the array) at a particular predetermined location (i.e., an "address") on the array will detect a particular sequence. Array features are typically, but need not be, separated by intervening spaces. In the case of an array in the context of the present application, the "population of labeled nucleic acids" or "labeled sample" and the like will be referenced as a moiety in a mobile phase (typically fluid), to be detected by "surface-bound nucleic acids" which are bound to the substrate at the various regions. These phrases are synonymous with the arbitrary terms "target" and "probe", or "probe" and "target", respectively, as they may be used in other publications.

A "scan region" refers to a contiguous (preferably, rectangular) area in which the array spots or features of interest, as defined above, are found or detected. Where fluorescent labels are employed, the scan region is that portion of the total area illuminated from which the resulting fluorescence is detected and recorded. Where other detection protocols are employed, the scan region is that portion of the total area queried from which resulting signal is detected and recorded. For the purposes of this invention and with respect to fluorescent detection embodiments, the scan region includes the entire area of the slide scanned in each pass of the lens, between the first feature of interest, and the last feature of interest, even if there exist intervening areas that lack features of interest.

An "array layout" refers to one or more characteristics of the features, such as feature positioning on the substrate, one or more feature dimensions, and an indication of a moiety at a given location. "Hybridizing" and "binding", with respect to nucleic acids, are used interchangeably.

The term "stringent assay conditions" as used herein refers to conditions that are compatible to produce binding pairs of nucleic acids, e.g., probes and targets, of sufficient complementarity to provide for the desired level of specificity in the assay while being incompatible to the formation of binding pairs between binding members of insufficient complementarity to provide for the desired specificity. The term stringent assay conditions refers to the combination of hybridization and wash conditions.

A "stringent hybridization" and "stringent hybridization wash conditions" in the context of nucleic acid hybridization (e.g., as in array, Southern or Northern hybridizations) are sequence dependent, and are different under different experimental parameters. Stringent hybridization conditions that can be used to identify nucleic acids within the scope of the invention can include, e.g., hybridization in a buffer comprising 50% formamide, 5×SSC, and 1% SDS at 42° C., or hybridization in a buffer comprising 5×SSC and 1% SDS at 65° C., both with a wash of 0.2×SSC and 0.1% SDS at 65° C. Hybridization buffers suitable for use in the methods described herein are well known in the art and may contain salt, buffer, detergent, chelating agents and other components at pre-determined concentrations.

The term "mixture", as used herein, refers to a combination of elements, that are interspersed and not in any particular order. A mixture is heterogeneous and not spatially separable into its different constituents. Examples of mixtures of elements include a number of different elements that are dissolved in the same aqueous solution, or a number of different elements attached to a solid support at random or in no particular order in which the different elements are not specially distinct. In other words, a mixture is not addressable. To be specific, an array of surface-bound oligonucleotides, as is commonly known in the art and described below, is not a mixture of surface-bound oligonucleotides because the species of surface-bound oligonucleotides are spatially distinct and the array is addressable.

"Isolated" or "purified" generally refers to isolation of a substance (compound, polynucleotide, protein, polypeptide, polypeptide composition) such that the substance comprises a significant percent (e.g., greater than 1%, greater than 2%, greater than 5%, greater than 10%, greater than 20%, greater than 50%, or more, usually up to about 90%-100%) of the sample in which it resides. In certain embodiments, a substantially purified component comprises at least 50%, 80%-85%, or 90-95% of the sample. Techniques for purifying polynucleotides and polypeptides of interest are well-known in the art and include, for example, ion-exchange chromatography, affinity chromatography and sedimentation according to density. Generally, a substance is purified when it exists in a sample in an amount, relative to other components of the sample, that is not found naturally.

The terms "determining", "measuring", "evaluating", "assessing" and "assaying" are used interchangeably herein to refer to any form of measurement, and include determining if an element is present or not. These terms include both quantitative and/or qualitative determinations. Assessing may be relative or absolute. "Assessing the presence of" includes determining the amount of something present, as well as determining whether it is present or absent.

The term "using" has its conventional meaning, and, as such, means employing, e.g., putting into service, a method or composition to attain an end. For example, if a program is used to create a file, a program is executed to make a file, the file usually being the output of the program. In another example, if a computer file is used, it is usually accessed, read, and the information stored in the file employed to attain an end. Similarly if a unique identifier, e.g., a barcode is used, the unique identifier is usually read to identify, for example, an object or file associated with the unique identifier.

If a subject nucleic acid probe "corresponds to" or is "for" a certain small RNA, the nucleic acid probe base pairs with, i.e., specifically hybridizes to, that small RNA. As will be discussed in greater detail below, a nucleic acid probe for a particular small RNA and the particular small RNA, or complement thereof, usually contain at least one region of contiguous nucleotides that is identical in sequence.

Description of the Specific Embodiments

The invention provides a nucleic acid probe for detecting a polynucleotide, e.g., a small RNA. The probe contains a region that base-pairs with a polynucleotide to form a duplex and a $T_m$ enhancement domain that increases the stability of the duplex. The $T_m$ enhancement domain may contain a nucleotide clamp and/or a hairpin structure, for example. Also provided is an array of subject nucleic acid probes bound to a surface of the solid support. Methods of using a subject probe to assess polynucteotides in a sample are provided, as are kits for use in practicing the subject methods. The invention finds use in a wide variety of diagnostic and research applications.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention.

Any recited method can be carried out in the order of events recited or in any other order which is logically possible.

In further describing the present invention, nucleic acid probes for detecting polynucleotides and arrays thereof will be described first, followed by a detailed description of how the subject nucleic acid probes may be used to assess polynucleotides in a sample. Finally, representative kits for use in practicing the subject methods will be discussed.

Nucleic Acid Probes

As mentioned above and with reference to FIG. 1, the invention provides a nucleic acid probe 2 for detecting a polynucleotide, e.g., a small RNA, containing: a first region 4 (i.e., a "binding region") that base-pairs with a small RNA to form a duplex; and a $T_m$ enhancement domain 6 that increases stability of the duplex. In certain embodiments, the nucleic acid probe 2 may be attached to a solid support 8, optionally via a linker 10. As will be described in greater detail below, the solid support may be part of an array, and the array may contain a plurality of different nucleic acid probes for detecting a plurality of polynucleotides.

As mentioned above, the nucleic acid probes of the invention may be used to detect any type of polynucleotide, including DNA (including oligonucleotides, genomic fragments and PCR products, or any fragmented version thereof, for example) and RNA (including small RNAs, cDNAs, rRNA, tRNA, or any fragmented version thereof, etc.). As will be described in greater detail below, the polynucleotide to be detected generally has a 3' end or 5' end (depending on which end of the nucleic acid for detecting that polynucleotide is attached to the solid support) of known sequence. The nucleic acid probes of the invention find particular use in detecting "small RNA" (or "short RNA" as it may also be referred to), where the terms "small RNA" and "short RNA" are used interchangeably herein as they are used in the art, i.e., to describe a group of non-coding regulatory RNAs that have defined sequences and that are in the range of 19-29 nucleotides (nts) in length. Many small RNAs are approximately 19-25 nts in length. Small RNAs are generally reviewed in Novina et al (Nature 2004 430:161-164) and may be classified in at least four groups: a) short interfering RNAs (siRNAs), b) micro-RNAs (miRNAs), c) tiny non-coding RNAs (tncRNAs) and d) small modulator RNAs (smRNAs). siRNAs are a class of double stranded RNAs of approximately 21-22 nt in length, generated from double stranded RNAs. siRNAs are thought to silence gene expression by promoting the cleavage of mRNAs. miRNAs, on the other hand, are a class of single stranded RNAs of approximately 19-25 nt in length. miRNAs appear to be evolutionary conserved and are thought to silence gene expression by inhibiting translation. tncRNAs are a class of RNAs that are about 20-22 nucleotides. tncRNAs appear to be developmentally regulated, although their function is unknown. smRNAs are double stranded RNAs involved in regulating neuron-specific gene expression in adult neurons. miRNAs are of particular interest. The sequences of several hundred miRNAs from a variety of different species, including humans, may be found at the microRNA registry (Griffiths-Jones, Nucl. Acids Res. 2004 32:D109-D111), as found at the world-wide website of the Sanger Institute (Cambridge, UK). The sequences of all of the microRNAs deposited at the microRNA registry, including 227 microRNA sequences from humans (see Lagos-Quintana et al, Science 294:853-858(2001); Grad et al, Mol Cell 11:1253-1263(2003); Mourelatos et al, Genes Dev 16:720-728(2002); Lagos-Quintana et al, Curr Biol 12:735-739 (2002); Lagos-Quintana et al, RNA 9:175-179(2003); Dostie et al, RNA 9:180-186(2003); Lim et al, Science 299:1540 (2003); Houbaviy et al, Dev Cell 5:351-358(2003); Michael et al, Mol Cancer Res 1:882-891(2003); Kim et al, Proc Natl Acad Sci U S A 101:360-365(2004); Suh et al, Dev Biol 270:488-498(2004); Kasashima et al, Biochem Biophys Res Commun 322:403-410(2004); and Xie et al, Nature 434:338-345(2005)), are incorporated herein by reference. The methods and compositions described above and below may be used to detect any of the microRNAs deposited at the microRNA registry, as well as others. As will be described in greater detail below, the nucleic acid probes described herein are particularly useful for the detection of shorter small RNAs, i.e., those small RNAs of 19-22 nt in length, although the subject nucleic acid probes may be employed to detect small RNAs of any length.

A subject nucleic acid probe may be in the range of about 10 to about 100 bases in length. In certain embodiments, however, a subject nucleic acid probe may be about 18 to about 70 bases, about 19 to about 60 bases, or about 20 to about 50 bases in length. As noted above, a subject nucleic acid probe generally contains a region 4 that base-pairs with a polynucleotide, e.g., a small RNA, to form a duplex and a duplex $T_m$ enhancement domain 6. Binding region 4 generally contains a contiguous nucleotide sequence that is complementary to the nucleotide sequence of a corresponding polynucleotide and is of a length that is sufficient to provide specific binding between the nucleic acid probe and the corresponding polynucleotide. Since small RNAs are generally in the range of 19-29 nt in length, region 4 is generally at least about 19 nt in length and in certain embodiments may be as long as 22 nt, 25 nt or 29 nt in length, or longer or, in certain embodiments, as short as 10-12 nucleotides. The nucleic acid probe, if it is attached to a solid support, may be attached via its 3' end or its 5' end. If the nucleic acid probe is attached to a solid support via its 3' end, the nucleotide at the 5' end of the first region of the nucleic acid probe generally base pairs with the 3' terminal nucleotide of a polynucleotide to be detected. Conversely, if the nucleic acid probe is attached to a solid support via its 5' end, the nucleotide at the 3' end of the first region of the nucleic acid probe generally base pairs with the 5' terminal nucleotide of a polynucleotide to be detected. A subject nucleic acid probe need not be complementary to the entire length of a corresponding polynucleotide to be detected, and a polynucleotide to be detected need not be complementary to the entire length of a subject nucleic acid probe.

The binding region 4 therefore corresponds to, i.e., hybridizes to and may be used to detect, a particular polynucleotide. In many einbodiments, the binding region is specific for a particular small RNA, i.e., is "small RNA-specific", in that it can detect a small RNA, even in the presence of other RNAs, e.g., other small RNAs. In other words, a subject nucleic acid probe contains a binding region that is complementary to a particular small RNA.

Figure 2A:
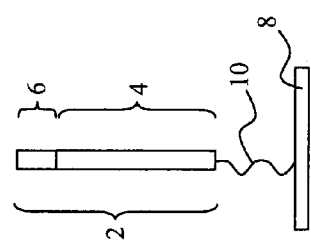
FIGS. 2A-2C schematically illustrate exemplary nucleic acid probes of the invention.
Figure 2B:
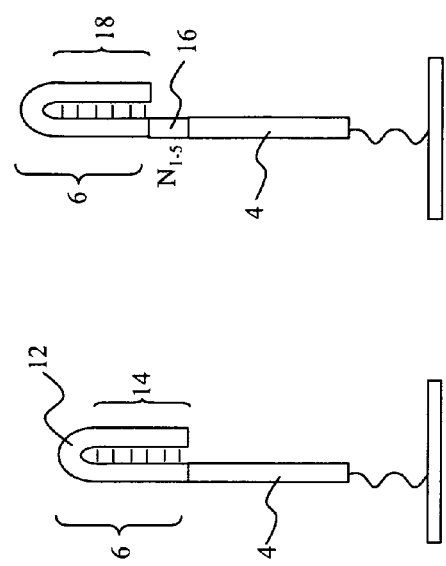
Figure 2C:
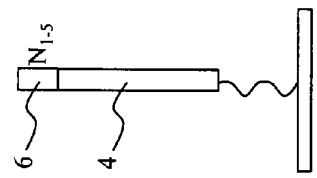

The $T_m$ enhancement domain of a subject nucleic acid probe, $T_m$ enhancement domain 6, increases the stability of the duplex formed by binding of a small RNA to region 4 of the nucleic acid probe. $T_m$ enhancement domain 6 may increase duplex stability via a number of mechanisms, including, for example, by providing a nucleotide clamp to which an extended polynucleotide, e.g., extended small RNA, may bind (as illustrated in FIG. 2A), or by providing a hairpin structure that increases stability via coaxial stacking (as illustrated in FIG. 2B). In certain embodiments and as illustrated in FIG. 2C, $T_m$ enhancement domain 6 may contain both a nucleotide clamp and a hairpin structure. Exemplary $T_m$ enhancement domain 6 are described in greater detail below. The sequence of the $T_m$ enhancement domain 6 is generally unrelated to the sequence of the binding region 4.

As mentioned above and as illustrated in FIG. 2A, $T_m$ enhancement domain 6 is immediately adjacent to binding region 4 and may contain a nucleotide clamp, where a nucleotide clamp contains a contiguous sequence of up to about 5 nucleotides (i.e., 1, 2, 3, 4 or 5 nucleotides). The identity of the nucteotides employed in the nucleotide clamp may be the same as each other or different to each other. As will be described in greater detail below and in certain embodiments, a subject nucleic acid probe containing a nucleotide clamp is employed in a method in which the polynucleotide to be detected by the nucleic acid probe is extended (in certain embodiments during labeling of the polynucleotide) to produce an extended small RNA. In the duplex formed between a polynucleotide probe containing a nucleotide clamp and an extended polynucleotide, the extended portion of the extended polynucleotide base-pairs with the $T_m$ enhancement domain 6 (i.e., the clamp) of the nucleic acid probe and the non-extended polynucleotide sequence base pairs with binding region 4. The addition of the nucleotide clamp increase the stability of the duplex, as compared to a duplex formed in the absence of the clamp. As would be apparent to one of skill in the art, the polynucleotide may be extended by nucleotides that are the same in number as and base pair with nucleotides that are present in the nucleotide clamp of the probe. A subject nucleic acid probe containing a nucleotide clamp is illustrated in FIG. 2A, where clamp region 6 contains $N_{1-5}$, wherein "N" is any nucleotide, particularly a G or a C. In a particular embodiment, a nucleotide clamp may contain one or two C or G residues. In other words and in certain embodiments, a subject nucleic acid probe may contain a first region that is complementary to at least 19 contiguous nucleotides at one end of a small RNA as well as a nucleotide clamp immediately adjacent to that region.

Depending on which end of the nucleic acid probe is attached to the solid support, nucleotide clamp 6 may be linked to the 3' end or 5' end of the binding region 4. In an embodiment of particular interest, the 3' end-of the nucleic acid probe is attached to the solid support and the 3' end of the nucleotide clamp is linked to the 5' end of binding region.

Figure 4C:
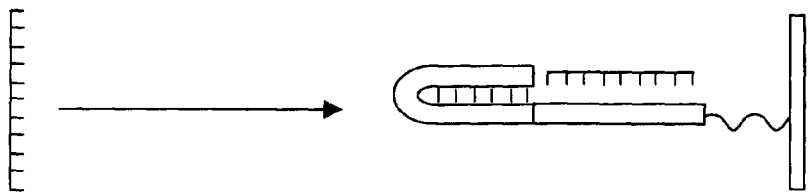
FIGS. 4A-4C schematically illustrate exemplary methods of the invention.
Figure 4B:
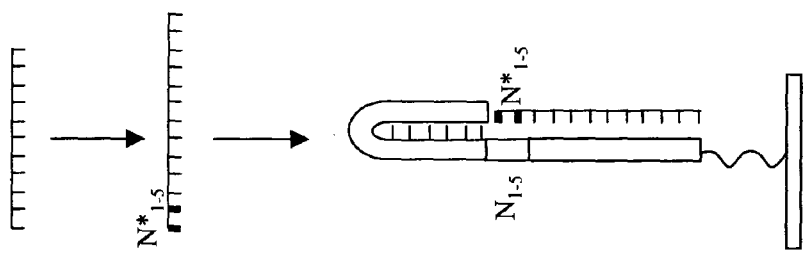

Also as mentioned above and as illustrated in FIG. 2B, $T_m$ enhancement domain 6 is immediately adjacent to binding region 4 and may contain a hairpin structure, where a hairpin structure has a loop 12 of at least 3 or 4 nucleotides and a double-stranded stem 14 in which complementary nucleotides bind to each other in an anti-parallel manner. The hairpin structure may contain from approximately 5 to about 30 nucleotides, e.g., about 8-20 nucleotides. The 5' terminal nucleotide of the hairpin generally base-pairs with the 3' terminal nucleotide of the hairpin, regardless of which end of the nucleic acid probe is bound to the solid support. In a duplex formed between a nucleic acid probe containing a hairpin region and a polynucleotide, the hairpin region promotes a phenomenon termed stacking (which phenomenon may also be called coaxial stacking) which allows the polynucleotide to bind more tightly, i.e., more stably. When labeled polynucleotide is bound to a nucleic acid probe containing a hairpin region, a terminal nucleotide of the labeled polynucleotide generally occupies a position that is immediately adjacent to a terminal nucleotide of the nucleic acid probe (as shown in FIG. 4B and 4C). In effect, in this embodiment, the duplex produced by binding of a labeled polynucleotide to a nucleic acid probe resembles a long hairpin structure containing a nick in the stem of the hairpin. Stacking and its effect on duplex stability are discussed in Liu et al (Nanobiology 1999; 4: 257-262), Walter et al (Proc. Natl. Acad. Sci. 1994 91:9218-9222) and Schneideretal (J. Biomol. Struct. Dyn. 2000 18:345-52), as well as many other references.

Depending on which end of the nucleic acid probe is attached to the solid support, hairpin structure 6 may be linked to the 3' or 5' end of the binding region 4. In an embodiment of particular interest, the 3' end of the nucleic acid probe is attached to the solid support and the 3' end of the hairpin is linked to the 5' end of binding region.

In certain embodiments and with reference to FIG. 2C, a nucleic acid probe of the invention may contain a $T_m$ enhancement domain 6 containing both a nucleotide clamp 16 and a hairpin structure 18. An extended polynucleotide bound to the nucleic acid probe of FIG. 2C is bound more tightly to the probe, as compared to the binding of the same polynucleotide to an equivalent nucleic acid probe solely containing a binding region 4.

The $T_m$ enhancement domain 6 effectively increases the stability (i.e., increases the tightness of binding and increases the melting temperature $T_m$) of a duplex containing a nucleic acid probe and a polynucleotide, as compared to the stability of a duplex obtained using a nucleic acid probe that does not contain the $T_m$ enhancement domain 6. The addition of the $T_m$ enhancement domain 6 to a nucleic acid probe for detecting a small RNA increases the $T_m$ of the probe by at least 1° C., and, in certain embodiments, by about 2° C., 3° C., 4° C. or 5° C. or more, up to about 10° C., as compared to an otherwise identical nucleic acid probe that does not contain the $T_m$ enhancement domain.

In addition to increasing the $T_m$ of a duplex, the use of a $T_m$ enhancement domain, particularly a hairpin structure, in a probe allows the probe to discriminate between different polynucleotides that are perfectly complementary to the probe. For example, as noted above, in representative embodiments a probe containing a hairpin region is designed so that the end of the probe (i.e., the end of the probe that is not attached to the solid support) is immediately adjacent to a terminal nucleotide of a polynucleotide when the polynucleotide is bound by the probe. This arrangement induces stacking, which, as explained above, increases the strength of binding between the nucleic acid probe and polynucleotide. If the terminal nucleotide of the polynucleotide does not lie immediately next to the nucleotide at the end of the probe (for example, if the polynucleotide is longer or shorter than the polynucleotide to be detected), then no stacking occurs. Accordingly, a subject hairpin structure-containing nucleic acid probe that is designed to detect a small RNA, in particular a miRNA, can discriminate between the small RNA and its precursor because only that small RNAs and not its precursor, when bound to such a nucleic acid probe, effects stacking. In other words, the hairpin structure provides for stearic hindrance of non-target polynucleotides.

Array Platforms

In certain embodiments of the invention a subject nucleic acid probe is a "surface-bound nucleic acid probe", where such a nucleic acid probe is bound, usually covalently but in certain embodiments non-covalently, to a surface of a solid substrate, i.e., a sheet, bead, or other structure. In certain embodiments, a surface-bound nucleic acid probe may be immobilized on a surface of a planar support, e.g., as part of an array.

A subject array may contain a plurality of features (i.e., 2 or more, about 5 or more, about 10 or more, about 15 or more, about 20 or more, about 30 or more, about 50 or more, about 100 or more, about 200 or more, about 500 or more, about 1000 or more, usually up to about 10,000 or about 20,000 or more features, etc.), each containing a different nucteic acid probe for detecting a small RNA. As few as one and as many as all of the nucleic acid probes of a subject array may contain a $T_m$ enhancement domain. In certain embodiments, at least 5%, at least 10% or at least 20% of the nucleic acid probes of an array contain a $T_m$ enhancement domain.

Different nucleic acid probes are present in different features of an array, i.e., spatially addressable areas of an array. In many embodiments a single type of nucleic acid probe is present in each feature (i.e., all the nucleic acid probes in the feature have the same sequence). However, in certain embodiments, the nucleic acids in a feature may be a mixture of nucleic acids having different sequences.

A subject array may contain a single nucleic acid probe. However, in certain embodiments, a subject array may contain a plurality of subject nucleic acid probes that correspond to (i.e., may be used to detect) a corresponding plurality of polynucleotides. In particular embodiments, the subject arrays may contain nucleic acid probes for detecting at least a portion all of the identified small RNAs of a particular organism.

In general, methods for the preparation of nucleic acid arrays, particularly oligonucleotide arrays, are well known in the art (see, e.g., Harrington et al,. Curr Opin Microbiol. (2000) 3:285-91, and Lipshutz et al., Nat Genet. (1999) 21:20-4) and need not be described in any great detail. The subject nucleic acid arrays can be fabricated using any means available, including drop deposition from pulse jets or from fluid-filled tips, etc, or using photolithographic means. Either polynucleotide precursor units (such as nucleotide monomers), in the case of in situ fabrication, or previously synthesized polynucleotides can be deposited. Such methods are described in detail in, for example U.S. Pat. Nos. 6,242,266, 6,232,072, 6,180,351, 6,171,797, 6,323,043, etc., the disclosures of which are herein incorporated by reference.

In certain embodiments and as will be described in greater detail below, an array of the invention may contain probes that all have a similar $T_m$. The spread of $T_m$s of such arrays may be less than about 10° C., less than about 5° C., or less than about 2° C., for example. The spread of $T_m$s of an array may be theoretically determined, or, in certain embodiments, experimentally determined.

Methods for Array Design

As noted above, the presence of a $T_m$ enhancement domain in a nucleic acid probe for detecting a polynucleotide of interest, e.g., a small RNA, increases the melting temperature of a duplex formed by a labeled polynucleotide and that nucleic acid probe. The ability to increase the melting temperature of such duplexes allows arrays having more favorable binding characteristics (as compared to arrays made using nucleic acid probes that do not contain stability sequences) to be designed and made. Accordingly, a nucleic acid probe for a polynucleotide may be designed and produced using the above-methods, and an array containing that nucleic acid probe may be fabricated.

In other words, the use of nucleic acid probes containing $T_m$ enhancement domains allows a set of nucleic acid probes for detecting polynucleotides, e.g., small RNAs, to be designed to have a lower $T_m$ spread (and, in certain embodiments, higher average $T_m$) than a set of nucleic acid probes that do not contain $T_m$ enhancement domains. The use of nucleic acid probes containing $T_m$ enhancement domains can increase the overall specificity of binding between a set of nucleic acid probes and labeled polynucleotide for those probes, leading to more accurate results. In one exemplary embodiment, the use of such arrays allows highly stringent hybridization conditions to be employed. For example, fewer ions, a higher hybridization temperature, a higher wash temperature or an extended wash period may be employed in hybridizing the subject arrays with a sample containing labeled polynucleotides, as compared to arrays containing otherwise identical nucleic acid probes that do not contain $T_m$ enhancement domains. For example, in hybridization of a subject array, salt concentration may be decreased or hybridization temperature may be increased in either the hybridization buffer employed or wash buffer employed, or both the hybridization and wash buffers employed for hybridization, as compared to an otherwise identical array that does not contain nucleic acid probes having stability sequences. A prolonged wash after the hybridization incubation may also be employed in the subject hybridization methods.

In one exemplary embodiments intended to exemplify but not limit this aspect of the invention, the sequences of a population of small RNAs (e.g., human or *Drosophila* miR-NAs, for example), are identified, and complementary polynucleotide sequences are designed to hybridize with those small RNAs. The $T_m$s of the complementary sequences are determined. In general terms, in order to provide a set of nucleic acid probes for those small RNAs, the sequence of the longer complementary polynucleotides are trimmed back to decrease their $T_m$s (e.g., by 1, 2, 3, 4, 5, 6, nucleotides or more, depending on the desired $T_m$), and $T_m$ enhancement domains are added to the shorter complementary polynucleotide sequences to increase their $T_m$s. An array containing the designed set of nucleic acid probes, at least some of which contain a $T_m$ enhancement domain, is then fabricated and the array is employed for the analysis of the population of small RNAs.

In alternative embodiments, particularly those embodiments in which a hairpin structure is employed as a $T_m$ enhancement domain, a $T_m$ enhancement domain may be added to all probes of an array, including both trimmed non-trimmed probes. The hairpin structure may assist in increasing probe specificity by preferentially binding to small RNAs, e.g., miRNAs, rather than pre-small RNAs (i.e., precursor RNAs that are cleaved to produce small RNAs, e.g., pre-miRNAs) in a sample. The presence of hairpin structure, in certain embodiments, allows a probe to discriminate between a small RNA and a precursor of that small RNA that is present in same sample.

Figure 3:
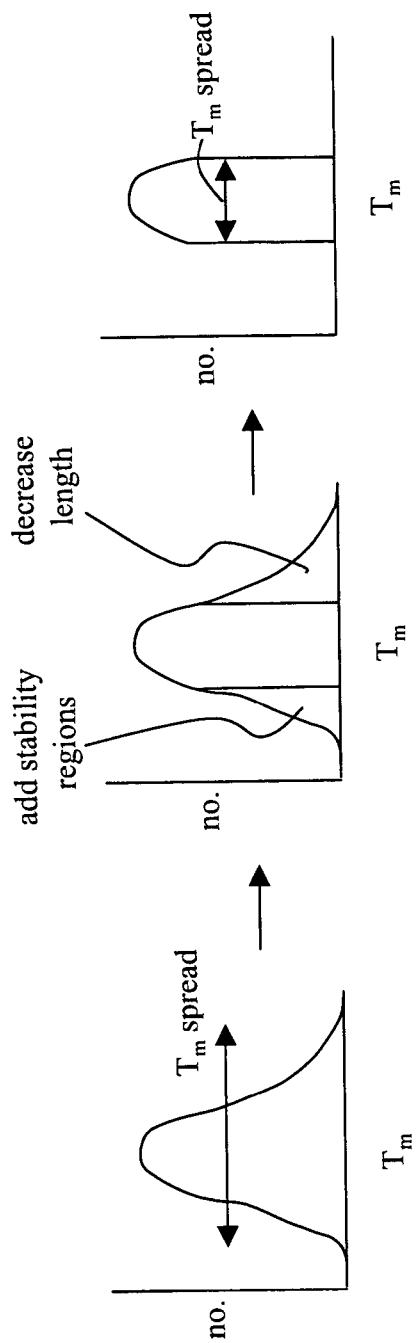
FIG. 3 schematically illustrate an embodiment of the invention.

As illustrated by the left hand graph of FIG. 3, the $T_m$s of the set of sequences complementary to the polynucleotides of a population of polynucleotides, e.g., small RNAs, are distributed across a $T_m$ spread (a $T_m$ spread being difference in temperature between the highest and lowest $T_m$ of the set). As illustrated in this graph, the $T_m$s may have an approximate normal distribution and form an approximate bell-shaped curve when plotted as shown. As illustrated in the middle graph of FIG. 3, in designing nucleic acid probes for the polynucleotides, the length of the complementary sequences having a higher $T_m$ is decreased (thereby decreasing the $T_m$ of those sequences) and stability sequences are added to the complementary sequences having a lower $T_m$ (thereby increasing the $T_m$ of those sequences). As illustrated in the right-hand graph of FIG. 3, once the $T_m$s of the population of complementary sequences have been adjusted by reducing the length of the sequences or by adding $T_m$ enhancement domains, the spread of the $T_m$s of the population is significantly reduced. Such a reduction in $T_m$ spread is highly desirable in microarray analysis.

Any nucleic acid probe designed according to the methods outlined above may be experimentally and/or computationally tested and altered until a nucleic acid probe having desired Tm is obtained. Methods for experimentally and computationally determining the $T_m$ of a nucleic acid duplex are well known in the molecular biology arts. In one embodiment, the Tm of a nucleic acid may be calculated using the methods described in U.S. patent application entitled "MELTING TEMPERATURE MATCHING", filed on Jul. 1, 2005, (attorney docket 10050948-01) which patent application is incorporated by reference herein.

Methods for Assessing Polynucleotides in a Sample

The subject invention provides a method of determining the amount of a polynucleotide, e.g., small RNA such as a particular miRNA, in a sample of polynucleotides that are labeled with a detectable label. In general, the method includes the following steps: a) contacting a subject nucleic acid probe with the sample under conditions sufficient for specific binding to occur between the nucleic acid probe and the labeled polynucleotides; and b) evaluating the presence of any detectable label associated with the nucleic acid probe, thereby evaluating the amount of the analyte in the sample.

In embodiments in which a nucleic acid probe containing a nucleotide clamp is employed, the polynucleotide of a sample of mixed polynucleotides may be extended to add nucleotides that are complementary to the nucleotide clamp of the nucleic acid probe. The addition of the nucleotides to the polynucleotides may be done before, simultaneously with or after labeling. In representative embodiment, a mononucleotide, di-nucleotide, tri-nucleotide, tetra-nucleotide or penta-nucleotide moiety is added to either the 3' or the 5' ends of the polynucleotides of a sample of polynucleotides using an enzyme, e.g., an RNA or DNA ligase or terminal transferase. A variety of RNA and DNA ligases may be purchased from a variety of vendors (e.g., Pharmacia, Piscataway, N.J., New England Biolabs, Berverly Ma., and Roche Diagnostics, Indianapolis, Ind.) and employed according to the instructions supplied therewith. In an embodiment of particular interest, the nucleotide(s) added to the polynucleotides are covalently linked to a label, e.g., a fluorophore, such that the polynucleotide is labeled by the addition of the fluorescent nucleotide. Labeled mononucleotides, di-nucleotides, tri-nucleotides, tetra-nucleotides, penta-nucleotides or higher order labeled polynucleotides are termed "nucleotide label moieties" herein.

Figure 4A:
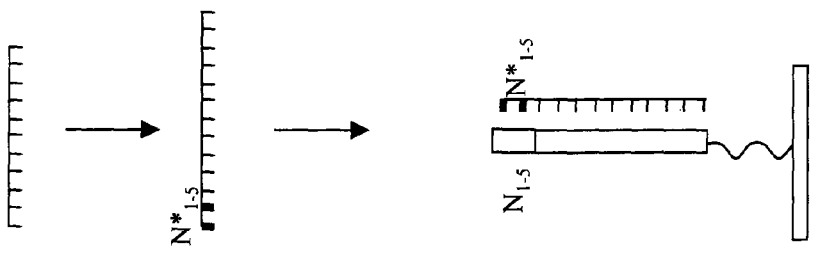

For example, and as illustrated in FIG. 4A, nucleotides ($N^*_{1-5}$) complementary to the nucleotide clamp of the nucleic acid probe are ligated to a terminus of a polynucleotide to produce a labeled polynucleotide. The labeled polynucleotide hybridizes to a nucleic acid probe containing a nucleotide clamp ($N_{1-5}$). The added nucleotides of the labeled polynucleotide base pair with the clamp of the nucleic acid probe whereas the remainder of the labeled polynucleotide base pair with the binding region of the probe. As illustrated in FIG. 4B, nucleotides ($N^*_{1-5}$) complementary to the nucleotide clamp of the nucleic acid probe are ligated to a terminus of a polynucleotide to produce a labeled polynucleotide. The labeled polynucleotide hybridizes to a nucleic acid probe containing a nucleotide clamp ($N_{1-5}$) and a hairpin. The added nucleotides of the labeled polynucleotide base pair with the clamp of the nucleic acid probe whereas the remainder of the labeled polynucleotide base pairs with the binding region of the probe. The coaxial stacking and the nucleotide clamping increase the stability of the duplex. Finally and with reference to FIG. 4C, a labeled polynucleotide hybridizes to a nucleic acid probe containing a hairpin structure. The labeled polynucleotide base pairs with the binding region of the probe and coaxial stacking increases the stability of the duplex.

In certain embodiments a subject array is employed to assess a sample of small RNAs that is prepared from a cell. Methods for preparing small RNAs from cells are well known in the art (see, e.g., Lagos-Quintana et al, Science 294:853-858(2001); Grad et al, Mol Cell 11:1253-1263 (2003); Mourelatos et al, Genes Dev 16:720-728(2002); Lagos-Quintana et al, Curr Biol 12:735-739(2002); Lagos-Quintana et al, RNA 9:175-179(2003) and other references cited above).

The sample is usually labeled to make a population of labeled nucleic acids. In general, a sample may be labeled using methods that are well known in the art (e.g., using DNA ligase, terminal transferase, or by labeling the RNA backbone, etc.; see, e.g., Ausubel, et al., Short Protocols in Molecular Biology, 3rd ed., Wiley & Sons 1995 and Sambrook et al., Molecular Cloning: A Laboratory Manual, Third Edition, 2001 Cold Spring Harbor, N.Y.), and, accordingly, such methods do not-need to be described here in great detail. In particular embodiments, the sample is usually labeled with fluorescent label, which labels will be described in greater detail below.

Fluorescent dyes of particular interest include: xanthene dyes, e.g. fluorescein and rhodamine dyes, such as fluorescein isothiocyanate (FITC), 6-carboxyfluorescein (commonly known by the abbreviations FAM and F),6-carboxy-2',4',7', 4,7-hexachlorofluorescein (HEX), 6-carboxy-4', 5'-dichloro-2', 7'-dimethoxyfluorescein (JOE or J), N,N,N',N'-tetramethyl-6-carboxyrhodamine (TAMRA or T), 6-carboxy-X-rhodamine (ROX or R), 5-carboxyrhodamine-6G ($R6G^5$ or $G^5$), 6-carboxyrhodamine-6G ($R6G^6$ or $G^6$), and rhodamine 110; cyanine dyes, e.g. Cy3, Cy5 and Cy7 dyes; Alexa dyes, e.g. Alexa-fluor-555; coumarins, e.g. umbelliferone; benzimide dyes, e.g. Hoechst 33258; phenanthridine dyes, e.g. Texas Red; ethidium dyes; acridine dyes; carbazole dyes; phenoxazine dyes; porphyrin dyes; polymethine dyes, e.g. cyanine dyes such as Cy3, Cy5, etc; BODIPY dyes and quinoline dyes. Specific fluorophores of interest that are commonly used in subject applications include: Pyrene, Coumarin, Diethylaminocoumarin, FAM, Fluorescein Chlorotriazinyl, Fluorescein, R110, Eosin, JOE, R6G, Tetramethylrhodamine, TAMRA, Lissamine, ROX, Napthofluorescein, Texas Red, Napthofluorescein, Cy3, and Cy5, etc.

After labeling, the labeled sample is contacted with a subject nucleic acid probe under conditions of stringency, usually high stringency, and any binding of labeled polynucleotide to a nucleic acid probe is detected by detecting the label associated with the nucleic acid probe.

In certain embodiments, binding of labeled small RNAs in the labeled sample is assessed with respect to binding of at least one control labeled sample. In one example, a suitable control labeled sample may be made from a control cell population, as will be described in greater detail below.

In certain embodiments, a sample and a control sample may be prepared and labeled, and relative binding of the labeled polynucleotides in the samples to a subject nucleic acid probe may be assessed. Since the subject nucleic acid probe may be a surface-bound nucleic acid probe that is present in a feature of an array, in many embodiments, the samples are labeled and contacted with at least one array containing a subject nucleic acid probe, under high stringency conditions.

In practicing the subject methods, the samples may be labeled to provide at least two different populations of labeled nucleic acids that are to be compared. The populations of nucleic acids may be labeled with the same label or different labels, depending on the actual assay protocol employed. For example, where each population is to be contacted with different but identical arrays, each nucleic acid population may be labeled with the same label. Alternatively, where both populations are to be simultaneously contacted with a single array of surface-bound nucleic acids, i.e., co-hybridized, to the same array of immobilized nucleic acids, target compositions are generally distinguishably labeled with respect to each other.

The samples are sometimes labeled using "distinguishable" labels in that the labels that can be independently detected and measured, even when the labels are mixed. In other words, the amounts of label present (e.g., the amount of fluorescence) for each of the labels are separately determinable, even when the labels are co-located (e.g., in the same tube or in the same duplex molecule or in the same feature of an array). Suitable distinguishable fluorescent label pairs useful in the subject methods include Cy-3 and Cy-5 (Amersham Inc., Piscataway, N.J.), Quasar 570 and Quasar 670 (Biosearch Technology, Novato Calif.), Alexafluor555 and Alexafluor647 (Molecular Probes, Eugene, Oreg.), BODIPY V-1002 and BODIPY V1005 (Molecular Probes, Eugene, Oreg.), POPO-3 and TOTO-3 (Molecular Probes, Eugene, Oreg.), fluorescein and Texas red (Dupont, Bostan Mass.) and POPRO3 and TOPRO3 (Molecular Probes, Eugene, Oreg.). Further suitable distinguishable detectable labels may be described in Kricka et al. (Ann Clin Biochem. 39:114-29, 2002).

Accordingly, in certain embodiments, at least a first population of small RNAs and a second population of small RNAs are produced from two different small RNA-containing samples, e.g., two populations of cells. As indicated above, depending on the particular assay protocol (e.g., whether both populations are to be hybridized simultaneously to a single array or whether each population is to be hybridized to two different but substantially identical, if not identical, arrays) the populations may be labeled with the same or different labels. As such, a feature of certain embodiments is that the different populations of labeled probe nucleic acids are labeled with the same label-such that they are not distinguishably labeled. In yet other embodiments, a feature of the different populations of labeled nucleic acids is that the first and second labels are distinguishable from each other.

After nucleic acid purification of labeled polynucleotides from unincorporated nucleotides, the populations of labeled polynucleotidez are usually contacted with an array of surface-bound nucleic acids, as discussed above, under conditions such that nucleic acid hybridization to the surface-bound nucleic acid probes can occur, e.g., in a buffer containing 50% formamide, 5×SSC and 1% SDS at 42° C., or in a buffer containing 5×SSC and 1% SDS at 65° C., both with a wash of 0.2×SSC and 0.1% SDS at 65° C., for example.

Standard hybridization techniques (using high stringency hybridization conditions) are used to probe a subject array. Suitable methods are described in many references (e.g., Kallioniemi et al., Science 258:818-821 (1992) and WO 93/18186). Several guides to general techniques are available, e.g., Tijssen, Hybridization with Nucleic Acid Probes, Parts I and II (Elsevier, Amsterdam 1993). For a descriptions of techniques suitable for in situ hybridizations see, Gall et al. Meth. Enzymol., 21:470-480 (1981) and Angerer et al. in Genetic Engineering: Principles and Methods Setlow and Hollaender, Eds. Vol. 7, pgs 43-65 (plenum Press, New York 1985). See also U.S. Pat. Nos: 6,335,167; 6,197,501; 5,830, 645; and 5,665,549; the disclosures of which are herein incorporate by reference.

Generally, the subject methods comprise the following major steps: (1) provision of an array containing surface-bound subject nucleic acid probes; (2) hybridization of a population of labeled polynucleotides to the surface-bound nucleic acid probes, typically under high stringency conditions; (3) post-hybridization washes to remove nucleic acids not bound in the hybridization; and (4) detection of the hybridized nucleic acids. The reagents used in each of these steps and their conditions for use vary depending on the particular application.

As indicated above, hybridization is carried out under suitable hybridization conditions, which may vary in stringency as desired. In certain embodiments, highly stringent hybridization conditions may be employed. The term "highly stringent hybridization conditions" as used herein refers to conditions that are compatible to produce nucleic acid binding complexes on an array surface between complementary binding members, i.e., between surface-bound subject nucleic acid probes and complementary labeled small RNAs in a sample. Representative high stringency assay conditions that may be employed in these embodiments are provided above.

The above hybridization step may include agitation of the immobilized targets and the sample of labeled nucleic acids, where the agitation may be accomplished using any convenient protocol, e.g., shaking, rotating, spinning, and the like.

Following hybridization, the surface of immobilized nucleic acids is typically washed to remove unbound labeled nucleic acids. Washing may be performed using any convenient washing protocol, where the washing conditions are typically stringent, as described above.

Following hybridization and washing-as described above, the hybridization of the labeled small nucleic acids to the array is then detected using standard techniques so that the surface of the array, is read. Reading of the resultant hybridized array may be accomplished by illuminating the array and reading the location and intensity of resulting fluorescence at each feature of the array to detect any binding complexes on the surface of the array. For example, a scanner may be used for this purpose that is similar to the AGILENT MICROARRAY SCANNER available from Agilent Technologies, Palo Alto, Calif. Other uitable devices and methods are described in U.S. patent applications Ser. No. 09/846125 "Reading Multi-Featured Arrays" by Dorsel et al.; and U.S. Pat. No. 6,406,849, which references are incorporated herein by reference. However, arrays may be read by any other method or apparatus than the foregoing, with other reading methods including other optical techniques (for example, detecting chemiluminescent or electroluminescent labels), or electrical techniques (where each feature is provided with an electrode to detect hybridization at that feature in a manner disclosed in U.S. Pat. No. 6,221,583 and elsewhere).

Results from the reading or evaluating may be raw results (such as fluorescence intensity readings for each feature in one or more color channels) or may be processed results (such as those obtained by subtracting a background measurement, or by rejecting a reading for a feature which is below a predetermined threshold, normalizing the results, and/or forming conclusions based on the pattern read from the array (such as whether or not a particular target sequence may have been present in the sample, or whether or not a pattern indicates a particular condition of an organism from which the sample came).

In certain embodiments, the subject methods include a step of transmitting data or results from at least one of the detecting and deriving steps, also referred to herein as evaluating, as described above, to a remote location. By "remote location" is meant a location other than the location at which the array is present and hybridization occur. For example, a remote location could be another location (e.g. office, lab, etc.) in the same city, another location in a different city, another location in a different state, another location in a different country, etc. As such, when one item is indicated as being "remote" from another, what is meant is that the two items are at least in different buildings, and may be at least one mile, ten miles, or at least one hundred miles apart.

"Communicating" information means transmitting the data representing that information as electrical signals over a suitable communication channel (for example, a private or public network). "Forwarding" an item refers to any means of getting that item from one location to the next, whether by physically transporting that item or otherwise (where that is possible) and includes, at least in the case of data, physically transporting a medium carrying the data or communicating the data. The data may be transmitted to the remote location for further evaluation and/or use. Any convenient telecommunications means may be employed for transmitting the data, e.g., facsimile, modem, internet, etc.

In certain embodiments, a level of binding of the labeled small RNA to a subject nucleic acid probe is assessed. The term "level of binding" means any assessment of binding (e.g. a quantitative or qualitative, relative or absolute assessment) usually done, as is known in the art, by detecting signal (i.e., pixel brightness) from the label associated with the labeled nucleic acids. Since the level of binding of labeled nucleic acid to a subject nucleic acid probe is proportional to the level of bound label, the level of binding of labeled nucleic acid is usually determined by assessing the amount of label associated with the feature.

In certain embodiments, a polynucleotide may be assessed by evaluating binding of a subject nucleic acid probe corresponding to that polynucleotide using two samples of polynucleotides that are distinguishably labeled. In these embodiments, for a single subject nucleic acid probe, the results obtained from hybridization with a first labeled sample may be compared to results obtained from the second label sample, usually after normalization of the data. The results may be expressed using any convenient means, e.g., as a number or numerical ratio, etc.

By "normalization" is meant that data corresponding to the two populations of polynucleotides are globally normalized to each other, and/or normalized to data obtained from controls (e.g., internal controls produce data that are predicted to equal in value in all of the data groups). Normalization generally involves multiplying each numerical value for one data group by a value that allows the direct comparison of those amounts to amounts in a second data group. Several normalization strategies have been described (Quackenbush et al, Nat Genet. 32 Suppl:496-501, 2002, Bilban et al Curr Issues Mol Biol. 4:57-64, 2002, Finkelstein et al, Plant Mol Biol.48 (1-2):119-31, 2002, and Hegde et al, Biotechniques. 29:548-554, 2000). Specific examples of normalization suitable for use in the subject methods include linear normalization methods, non-linear normalization methods, e.g., using lowess local regression to paired data as a function of signal intensity, signal-dependent non-linear normalization, qspline normalization and spatial normalization, as described in Workman et al., (Genome Biol. 2002 3, 1-16). In certain embodiments, the numerical value associated with a feature signal is converted into a log number, either before or after normalization occurs. Data may be normalized to data obtained using a support-bound polynucleotide probe for a polynucleotide of known concentration, for example.

Accordingly, since the arrays used in the subject assays may contain nucleic acid probes for a plurality of different polynucleotides, the presence of a plurality of different polynucleotides may be assessed. The subject methods are therefore suitable for simultaneous assessment of a plurality of polynucleotides in a sample.

Computer-Related Embodiments

The invention also provides a variety of computer-related embodiments. Specifically, the methods of designing a set of nucleic acid probes for use in an array to analyze small RNAs in a sample may be performed using a computer. Accordingly, the invention provides a computer-based system for designing a set of nucleic acid probes using the above methods.

In many embodiments, the methods are coded onto a computer-readable medium in the form of "programming", where the term "computer readable medium" as used herein refers to any storage or transmission medium that participates in providing instructions and/or data to a computer for execution and/or processing. Examples of storage media include floppy disks, magnetic tape, CD-ROM, a hard disk drive, a ROM or integrated circuit, a magneto-optical disk, or a computer readable card such as a PCMCIA card and the like, whether or not such devices are internal or external to the computer. A file containing information may be "stored" on computer readable medium, where "storing" means recording information such that it is accessible and retrievable at a later date by a computer.

With respect to computer readable media, "permanent memory" refers to memory that is permanent. Permanent memory is not erased by termination of the electrical supply to a computer or processor. Computer hard-drive ROM (i.e. ROM not used as virtual memory), CD-ROM, floppy disk and DVD are all examples of permanent memory. Random Access Memory (RAM) is an example of non-permanent memory. A file in permanent memory may be editable and re-writable.

A "computer-based system" refers to the hardware means, software means, and data storage means used to analyze the information of the present invention. The minimum hardware of the computer-based systems of the present invention comprises a central processing unit (CPU), input means, output means, and data storage means. A skilled artisan can readily appreciate that any one of the currently available computer-based system are suitable for use in the present invention. The data storage means may comprise any manufacture comprising a recording of the present information as described above, or a memory access means that can access such a manufacture.

To "record" data, programming or other information on a computer readable medium refers to a process for storing information, using any such methods as known in the art. Any convenient data storage structure may be chosen, based on the means used to access the stored information. A variety of data processor programs and formats can be used for storage, e.g. word processing text file, database format, etc.

A "processor" references any hardware and/or software combination which will perform the functions required of it. For example, any processor herein may be a programmable digital microprocessor such as available in the form of a electronic controller, mainframe, server or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic medium or optical disk may carry the programming, and can be read by a suitable reader communicating with each processor at its corresponding station.

Kits

Also provided by the subject invention are kits for practicing the subject methods, as described above. The subject kits contain at least a subject nucleic acid probe. The nucleic acid probe may be bound to the surface of a solid support and may be present in an array. The kit may also contain reagents for isolating small RNAs from a cell, reagents for labeling a small RNA, reagents for hybridizing labeled small RNAs to an array, a control small RNA, etc. The various components of the kit may be present in separate containers or certain compatible components may be precombined into a single container, as desired.

In addition to above-mentioned components, the subject kits may further include instructions for using the components of the kit to practice the subject methods, i.e., to instructions for sample analysis. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g., CD-ROM, diskette, etc. In yet other embodiments, the actual instructions are not present in the kit, but means for obtaining the instructions from a remote source, e.g., via the internet, are provided. An example of this embodiment is a kit that includes a web address where the instructions can be viewed and/or from which the instructions can be downloaded. As with the instructions, this means for obtaining the instructions is recorded on a suitable substrate.

Utility

The subject methods may be employed in a variety of diagnostic, drug discovery, and research applications that include, but are not limited to, diagnosis or monitoring of a disease or condition (where the expression of a particular small RNA is a marker for the disease or condition), discovery of drug targets (where the small RNA is differentially expressed in a disease or condition and may be targeted for drug therapy), drug screening (where the effects of a drug are monitored by assessing the level of a small RNA), determining drug susceptibility (where drug susceptibility is associated with a particular profile of small RNAs) and basic research (where is it desirable to identify the presence of small RNAs in a sample, or, in certain embodiments, the relative levels of a particular small RNA in two or more samples).

In certain embodiments, relative levels of small RNAs in two or more different small RNA samples may be obtained using the above methods, and compared. In these embodiments, the results obtained from the above-described methods are usually normalized to the total amount of RNA in the sample or to control RNAs (e.g., constitutive RNAs), and compared. This may be done by comparing ratios, or by any other means. In particular embodiments, the small RNA profiles of two or more different samples may be compared to identify small RNA that are associated with a-particular disease or condition (e.g., a small RNA that that is induced by the disease or condition and therefore may be part of a signal transduction pathway implicated in that disease or condition).

The different samples may consist of an "experimental" sample, i.e., a sample of interest, and a "control" sample to which the experimental sample may be compared. In many embodiments, the different samples are pairs of cell types or fractions thereof, one cell type being a cell type of interest, e.g., an abnormal cell, and the other a control, e.g., normal, cell. If two fractions of cells are compared, the fractions are usually the same fraction from each of the two cells. In certain embodiments, however, two fractions of the same cell may be compared. Exemplary cell type pairs include, for example, cells isolated from a tissue biopsy (e.g., from a tissue having a disease such as colon, breast, prostate, lung, skin cancer, or infected with a pathogen etc.) and normal cells from the same tissue, usually from the same patient; cells grown in tissue culture that are immortal (e.g., cells with a proliferative mutation or an immortalizing transgene), infected with a pathogen, or treated (e.g., with environmental or chemical agents such as peptides, hormones, altered temperature, growth condition, physical stress, cellular transformation, etc.), and a normal cell (e.g., a cell that is otherwise identical to the experimental cell except that it is not immortal, infected, or treated, etc.); a cell isolated from a mammal with a cancer, a disease, a geriatric mammal, or a mammal exposed to a condition, and a cell from a mammal of the same species, preferably from the same family, that is healthy or young; and differentiated cells and non-differentiated cells from the same mammal (e.g., one cell being the progenitor of the other in a mammal, for example). In one embodiment, cells of different types, e.g., neuronal and non-neuronal cells, or cells of different status (e.g., before and after a stimulus on the cells) may be employed. In another embodiment of the invention, the experimental material is cells susceptible to infection by a pathogen such as a virus, e.g., human immunodeficiency virus (HIV), etc., and the control material is cells resistant to infection by the pathogen. In another embodiment of the invention, the sample pair is represented by undifferentiated cells, e.g., stem cells, and differentiated cells.

Cells from yeast, plants and animals, such as fish, birds, reptiles, amphibians and mammals may be used in the subject methods. In certain embodiments, mammalian cells, i.e., cells from mice, rabbits, primates, or humans, or cultured derivatives thereof, may be used.

Accordingly, among other things, the instant methods may be used to link the expression of certain genes to certain physiological events.

The following examples are offered by way of illustration and not by way of limitation.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Array Fabrication

Three *Drosophila* miRNAs were chosen for analysis: miR-14, let-7 and miR-31A. Nucleic acid probes containing: a) neither a nucleotide clamp nor a hairpin structure (indicated by "S"), b) a 5' single nucleotide clamp (indicated by "G") and c) a 5' single nucleotide clamp and a hairpin structure (indicated by "H") were designed: dme-miR-14(S) TAG-GAGAGAGAAAAAGACTGAXXXXXXXXXX (SEQ ID NO:1); dme-miR-14(H) CGCTCGGGTTTTCCCGAGCG-GTAGGAGAGAGAAAAAGACTGAXXXXXXXXXX (SEQ ID NO:2); dme-miR-14(G) GTAG-GAGAGAGAAAAAGACTGAXXXXXXXXXX (SEQ ID NO:3); dme-let-7(S) ACTATACAACCTACTACCT-CAXXXXXXXXXX (SEQ ID NO:4); dme-let-7(H) CGCTCGGGTTTTCCCGAGCGGACTATA- CAACCTACTACCTCAXXXXXXXXXX (SEQ ID NO:5); dme-let-7(G) GACTATACAACCTACTACCT-CAXXXXXXXXXX (SEQ ID NO:6); dme-miR-31a(S) TCAGCTATGCCGACATCTTXXXXXXXXXX (SEQ ID NO:7); dme-miR-31a(H) CGCTCGGGTTTTCCCGAGCG-GTCAGCTATGCCGACATCTTXXXXXXXXXX (SEQ ID NO:8); dme-miR-31a(G) GTCAGCTATGCCGACATCT-TXXXXXXXXXX (SEQ ID NO:9), wherein "X" is a nucleotide linker, in this case T residue. The nucleic acid probes were linked by their 3' ends to the surface of a glass slide in the form of an array. The array was blocked and prepared for hybridization using standard methods.

Example 2

RNA Ligation

RNA ligation was assessed with synthetic RNA oligonucleotides (21-23 nucleotides, Dharmacon) in reaction solutions containing 0,15,20,25, and 30% DMSO. The reactions containing 25% DMSO were assays with and without preheating. 20 uM RNA oligo stocks were stored in 1X TE (10 mM Tris-HCl, pH 7.5, 1 mM EDTA). Initial mixtures of RNA, DMSO and water were first assembled. For pre-heated samples, the heated mixture contained 40-70% DMSO and were heated in 104° C. heating block for 1.5-2 minutes. The heated samples were immediately set on ice for >5 minutes prior to final assembly. The final reaction contains 1X Amersham Pharmacia RNA ligase buffer (50 mM Tris-HCl, pH 7.5, 10 mM MgCl2, 10 mM DTT, 1 mM ATP, 60 ng/uL BSA) 1unit/uL T4 RNA ligase, 100 uM, 5'-phosphate-cytidyl-phosphate-Cy5-3' (pCpCy5) or 5'-phosphate-cytidyl-phosphate-Cy3-3'(pCpCy3) (Dharmacon) and 2-4 uM RNA oligonucleotides. The reactions were incubated at 16° C. overnight. RNA ligase was inactivated by heating to 104° C. and immediate freezing.

The labeling efficiency was determined by 5' phosphorylation of RNA ligation reaction aliquots with radioactive $P^{32}$-gamma-ATP. The resulting mixture was desalted with Micro-BioSpin (BioRad) desalting columns. The desalted mixture was loaded onto denaturing polyacrylamide gel. Since the ligation products contain an extra nucleotide and fluorephore, they have a lower electrophoretic migration rate than the unligated precursors. $P^{32}$-labeled RNA bands are visualized and quantified with phosphorimager (Molecular Dynamics). The ligation efficiency was determined by the ratio of ligated vs unligated $P^{32}$-labeled RNA bands.

Hybridization

The RNA sample is mixed with hybridization buffer. The sample is heated to 45° C.-106° C., immediately cooled on ice and added to the microarray. The hybridization is carried out at the desired temperature (50° C.-65° C.) for a desired time (12-26 hours). The hybridization chamber is disassembled in wash buffer containing 6X SSC, 0.005% Trition X-102. It is then transferred to fresh buffer of the same composition and washed for 10 minutes at room temperature. This is followed by a wash in 0.1X SSC and 0.005% Triton X-102 for 5 minutes at room temperature. The microarray slide is then dried and scanned.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarit of understanding, it is readily apparent to those of ordinary skill in the art in light of the teachings of this invention that certain changes and modifications may be made thereto without departing from the spirit or scope of the appended claims.

What is claimed is:

1. A nucleic acid duplex, comprising a polynucleotide and a probe that are base-paired with each other,
    a) wherein said polynucleotide-comprises a labeled nucleotide added to the 3'end of said polynucleotide; and
    b) wherein said probe comprises:
        i) a region that is base-paired with said polynucleotide to form a duplex; and
        ii) a $T_m$ enhancement domain comprising: a) a nucleotide clamp that is base-paired with said labeled nucleotide and b) a hairpin region, wherein said $T_m$ enhancement domain increases stability of said duplex via coaxial stacking, and wherein said probe is bound to a surface of a solid support by its 3' terminus.

2. The nucleic acid duplex of claim 1, wherein said polynucleotide is a small RNA selected from the group consisting of a short interfering RNA (siRNA), microRNA (miRNA), tiny non-coding RNA (tncRNA) and a small modulatory RNA (smRNA).

3. The nucleic acid duplex of claim 1, wherein said hairpin region provides for steric hindrance for non-target polynucleotides.

4. The nucleic acid probe of claim 1, wherein said polynucleotide is a fragment of an RNA.

5. The nucleic acid probe of claim 4, wherein said fragment is a fragment of a tRNA, mRNA or a rRNA.

6. An array comprising:
    a) a solid support having a surface; and
    b) at least one nucleic acid probe for detecting a polynucleotide comprising a labeled nucleotide added to the 3'end of said polynucleotide, wherein said nucleic acid probe comprises:
        i) a region that base-pairs with said polynucleotide to form a duplex; and
        ii) a $T_m$ enhancement domain comprising: a) a nucleotide clamp that base-pairs with said labeled nucleotide and b) a hairpin region, wherein said $T_m$ enhancement domain increases stability of said duplex via coaxial stacking, wherein said at least one nucleic acid probe is bound to said surface by its 3' terminus.

7. The array of claim 6, wherein said at least one nucleic acid probe is present on said surface as a discrete feature.

8. The array of claim 6, wherein said at least one nucleic acid probe comprises a linker between said region and said surface.

9. A kit for assessing polynucleotides in a polynucleotide sample, comprising:
    a) reagents for adding a labeled nucleotide to the 3' end of a polynucleotide;
    b) a nucleic acid probe for detecting polynucleotide, wherein said nucleic acid probe comprises:
        i) a region that base-pairs with said polynucleotide to form a duplex; and
        ii) a $T_m$ enhancement domain comprising: a) a nucleotide clamp that base-pairs with said labeled nucleotide and b) a hairpin region that does not hybridize to said polynucleotide under stringent hybridization conditions, wherein said $T_m$ enhancement domain increases stability of said duplex via coaxial stacking, wherein said nucleic acid probe is bound to a surface of a solid support by its 3' terminus; and c) instructions for using said nucleic acid probe to assess polynucleotides in said polynucleotide sample.

10. The kit of claim 9, wherein said kit contains control polynucleotides.

11. The kit of claim 9, further comprising reagents for isolating polynucleotides from a cell.

12. The kit of claim 9, further comprising reagents for labeling said polynucleotide.

13. The kit of claim 9, wherein said labeling reagents distinguishably label polynucleotides in two samples.

14. The kit of claim 9, wherein said nucleic acid probe is bound to a surface of a solid support and is part of an array of nucleic acid probes.

\* \* \* \* \*

UNITED STATES PATENT AND TRADEMARK OFFICE
CERTIFICATE OF CORRECTION

| | | |
|---|---|---|
| PATENT NO. | : 9,297,036 B2 | Page 1 of 2 |
| APPLICATION NO. | : 11/173693 | |
| DATED | : March 29, 2016 | |
| INVENTOR(S) | : Hui Wang | |

It is certified that error appears in the above-identified patent and that said Letters Patent is hereby corrected as shown below:

On the title page, in item (56), in column 2, under "Other Publications", line 1, delete "labeleing" and insert -- labeling --, therefor.

On the title page, in item (56), in column 2, under "Other Publications", line 4, delete "Secification" and insert -- Specification --, therefor.

On the title page, in item (56), in column 2, under "Other Publications", line 9, delete "tisues," and insert -- tissues, --, therefor.

On the title page 2, in column 1, under "Other Publications", line 6, delete "Reseach," and insert -- Research, --, therefor.

On the title page 2, in column 1, under "Other Publications", line 7, delete ""Micorarray" and insert -- "Microarray --, therefor.

In the Specification

In column 1, line 15, delete "fuinctions" and insert -- functions --, therefor.

In column 3, line 23, delete "otigonucleotides." and insert -- oligonucleotides. --, therefor.

In column 6, line 16, delete "polynucteotides" and insert -- polynucleotides --, therefor.

In column 8, line 47, delete "einbodiments," and insert -- embodiments, --, therefor.

In column 9, line 6, delete "nucteotides" and insert -- nucleotides --, therefor.

In column 9, line 66, delete "Schneideretal" and insert -- Schneider et al. --, therefor.

In column 10, line 44, delete "RNA,_in" and insert -- RNA, in --, therefor.

In column 10, line 64, delete "nucteic" and insert -- nucleic --, therefor.

In column 13, line 29, delete "Berverly" and insert -- Beverly --, therefor.

In column 13, line 37, delete "termied" and insert -- termed --, therefor.

In column 14, line 34, delete "Napthofluorescein," and insert -- Naphthofluorescein, --, therefor.

In column 14, line 35, delete "Napthofluorescein," and insert -- Naphthofluorescein, --, therefor.

Signed and Sealed this
Seventh Day of June, 2016

Michelle K. Lee
*Director of the United States Patent and Trademark Office*

CERTIFICATE OF CORRECTION (continued)
U.S. Pat. No. 9,297,036 B2

In column 16, line 21, delete "washing-as" and insert -- washing, as --, therefor.

In column 16, line 31, delete "uitable" and insert -- suitable --, therefor.

In column 19, line 49, delete "a-particular" and insert -- a particular --, therefor.

In column 19, line 50, delete "that that" and insert -- that --, therefor.

In column 21, lines 31-32, delete "5'-phosphate-cytidyl-phosphate-Cy5-3'" and insert -- 5'-phosphate-cytidine-phosphate-Cy5-3' --, therefor.

In column 21, lines 32-33, delete "5'-phosphate-cytidyl-phosphate-Cy3-3'" and insert -- 5'-phosphate-cytidine-phosphate-Cy3-3' --, therefor.

In column 21, line 42, delete "fluorephore," and insert -- fluorophore, --, therefor.

In column 21, line 56, delete "Trition" and insert -- Triton --, therefor.

In column 22, line 5, delete "clarit" and insert -- clarity --, therefor.